(12) United States Patent
Knötzel et al.

(10) Patent No.: US 8,101,376 B2
(45) Date of Patent: Jan. 24, 2012

(54) SWATCH FOR TESTING THE WASHING PERFORMANCE OF AN ENZYME

(75) Inventors: Jürgen Carsten Franz Knötzel, Copenhagen Oe (DK); Jytte Poulsen, Valby (DK)

(73) Assignee: Novozymes A/S, Bagsvaerd (DK)

( * ) Notice: Subject to any disclaimer, the term of this patent is extended or adjusted under 35 U.S.C. 154(b) by 159 days.

(21) Appl. No.: 11/915,186

(22) PCT Filed: May 22, 2006

(86) PCT No.: PCT/DK2006/000279
§ 371 (c)(1),
(2), (4) Date: Nov. 21, 2007

(87) PCT Pub. No.: WO2006/125437
PCT Pub. Date: Nov. 30, 2006

(65) Prior Publication Data
US 2008/0280315 A1    Nov. 13, 2008

Related U.S. Application Data

(60) Provisional application No. 60/686,182, filed on Jun. 1, 2005.

(30) Foreign Application Priority Data

May 27, 2005    (DK) ................................ 2005 00775

(51) Int. Cl.
*C12Q 1/44* (2006.01)
*C12Q 1/37* (2006.01)
*C12Q 1/34* (2006.01)
*C12Q 1/00* (2006.01)
*C12N 9/00* (2006.01)

(52) U.S. Cl. .................. 435/19; 435/23; 435/18; 435/4; 435/183

(58) Field of Classification Search .................... 435/19, 435/23, 18, 4, 183
See application file for complete search history.

(56) References Cited

U.S. PATENT DOCUMENTS

| 4,394,444 A | * | 7/1983 | Cameron et al. | 435/11 |
| 5,064,440 A | * | 11/1991 | Howard et al. | 8/137 |
| 5,556,743 A | * | 9/1996 | Gibboni et al. | 435/4 |

FOREIGN PATENT DOCUMENTS

| WO | WO 99/34011 | 7/1999 |
| WO | WO 00/01842 | 1/2000 |
| WO | WO 02/42740 | 5/2002 |

OTHER PUBLICATIONS

Aaslyng et al., "Mechanistic Studies of Proteases and Lipases for the Detergent Industry", Journal of Chemical Technology and Biotechnology, Wiley & Sons, Chichester, GB, pp. 321-330 (1991).

* cited by examiner

*Primary Examiner* — Ganapathirama Raghu
(74) *Attorney, Agent, or Firm* — Elias Lambiris

(57) ABSTRACT

The present invention relates to a swatch comprising a pH-indicator substance and a substrate for an enzyme for testing the washing performance of the enzyme, e.g. an enzyme for use in detergent compositions.

13 Claims, 13 Drawing Sheets

SWATCH FOR TESTING THE WASHING PERFORMANCE OF AN ENZYME

CROSS-REFERENCE TO RELATED APPLICATIONS

This application is a 35 U.S.C. 371 national application of PCT/DK2006/000279 filed May 22, 2006, which claims priority or the benefit under 35 U.S.C. 119 of Danish application no. PA 2005 00775 filed May 27, 2005 and U.S. provisional application no. 60/686,182 filed Jun. 1, 2005, the contents of which are fully incorporated herein by reference.

TECHNICAL FIELD

The present invention relates to a swatch for testing the washing performance of an enzyme, e.g. for use in detergent compositions.

BACKGROUND OF THE INVENTION

Enzymes, e.g., proteases, amylases, lipases, cellulases, peroxidases/oxidases are well known ingredients in cleaning and detergent agents because of their ability to break down conventional substances of dirt. When developing enzymes there is a need to determine and compare the washing performance of different enzymes. Washing performance is usually tested by subjecting fabrics stained with suitable compounds in a standardised way with detergent compositions containing the enzymes to be tested. WO 02/42740 discloses an automated assay for determining the washing performance of cleaning and detergent ingredients e.g. enzymes and/or combinations of enzymes. Some detergent enzymes, e.g. lipases, may be active in the clothes after washing and during drying. This may be desirous under some circumstances since it may improve the washing performance, but may not be desirous under other circumstances since it may lead to formation of malodour due to release of fatty acids.

There is a need for an improved swatch and method for testing the washing performance of enzymes and the activity of the washing enzymes during drying.

SUMMARY OF THE INVENTION

Consequently, the present invention relates to a swatch for testing the washing performance of an enzyme, comprising a pH-indicator substance and a substrate for the enzyme, wherein conversion of the substrate by the enzyme will lead to a change in pH. Additionally, the present invention relates to a method for testing the washing performance of an enzyme, and a method for testing the activity of an enzyme during drying of a swatch.

DETAILED DISCLOSURE OF THE INVENTION

Swatch

Figure 1:
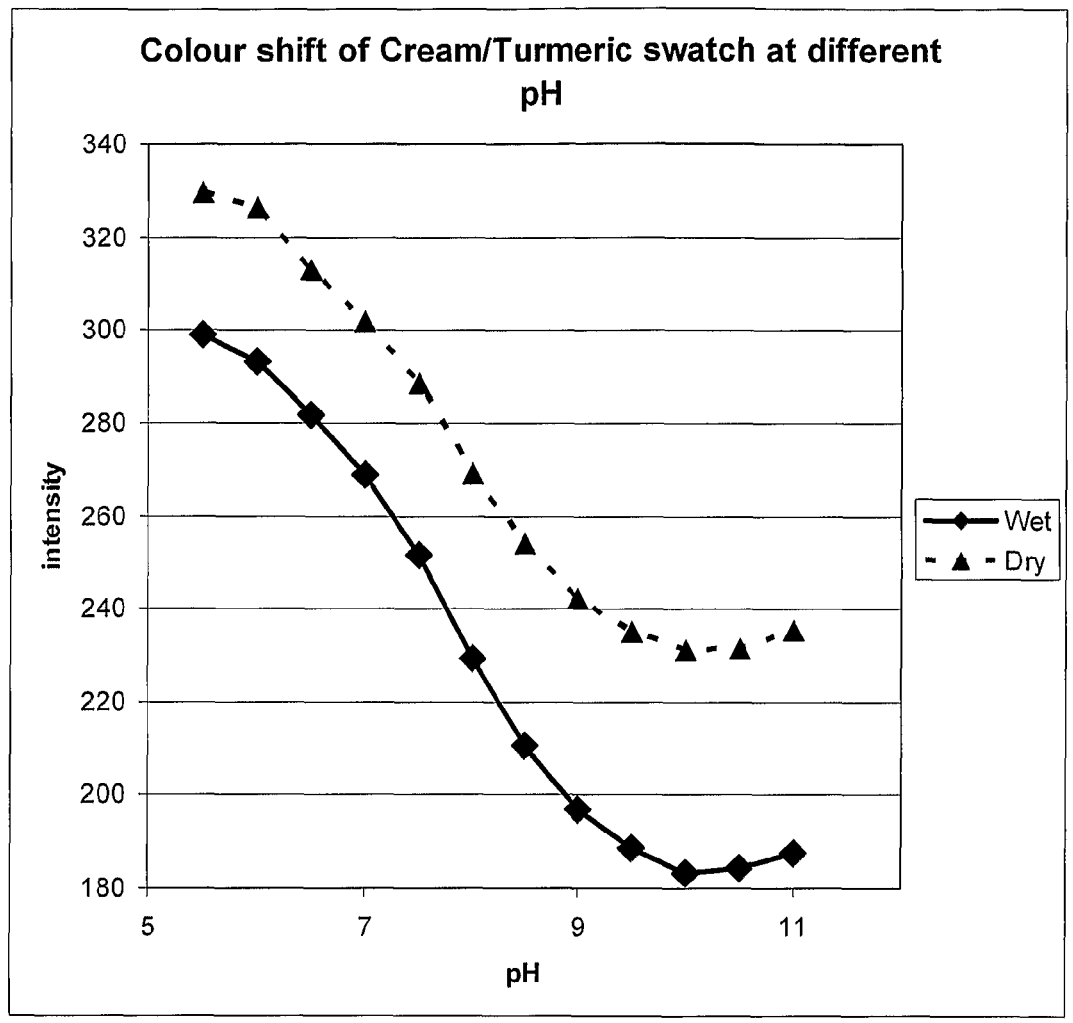
FIG. 1 shows Cream/turmeric swatch after AMSA (Automated Mechanical Stress Assay) with buffers of pH 5.5 to pH 11.0. The pH of the buffer leads to colour change of the swatch. Decreasing pH values are responsible for an increase of intensity values.

In the present context a swatch is a piece of fabric such as conventional fabrics that may be used for manufacture of clothes and subjected to washing processes. The fabric may be any fabric made from natural plant fibres, e.g. cotton and linen; animal based fibres, e.g. wool and silk; or synthetic fibres, e.g. acrylic, polyester, polyamide, and elastane; or combinations thereof. The fabric may be woven or non-woven or soft or stiff. Preferred fabrics are cellulose containing fabrics such as textiles (woven) and tissues (non woven) and animal based fabrics such as wool.

Substrate

The substrate may be any substrate that can be converted by an enzyme and where the conversion leads to a change in pH. In one embodiment the substrate is triglyceride. Triglycerides may be hydrolysed by enzymes with lipase activity into free fatty acids and glycerol. The release of free fatty acids will result in a lowering of pH by dissociation of hydrogen ions. Triglycerides may e.g. be present as edible oil or fat, e.g. from vegetable or animal source. Animal fat may e.g. be milk fat, e.g. in the form of cream, butter, or free milk fat. If the substrate comprises triglycerides the swatch may be used to assess the washing performance of enzymes with lipase activity. Enzymes with lipase activity are capable of hydrolysing triglycerides by releasing free fatty acids. This reaction leads to a decrease in pH.

In another embodiment the substrate is protein. Protein may be hydrolysed by enzymes having proteolytic activity into peptides and amino acids. Hydrogen ions released by proteolysis of protein lead to a decrease of pH. In one embodiment of the invention the substrate is protein.

pH-Indicator Substance

The pH-indicator substance may be any substance that change colour as a result of a change in pH. The colour change may be detectable at any wavelength, e.g. within the visual spectrum, the infrared spectrum, and/or the ultraviolet spectrum, or fluorescence. In a preferred embodiment the colour change can be detected in the visual spectrum. Preferably the pH-indicator substance is bound to, or has affinity to, the substrate and/or the swatch material, so that the pH-indicator substance is not completely removed from the swatch by the rinsing steps of the method of the invention. If the substrate is oil or fat, the pH-indicator substance may e.g. be lipophilic.

In one embodiment of the invention the pH-indicator substance is turmeric (*Curcuma longa*), e.g. in the form of crushed root of *Curcuma longa*. Curcumin ((E,E)-1,7-bis(4-Hydroxy-3-methoxyphenyl)-1,6-heptadiene-3,5-dione; synonyms: Diferuloylmethane, Diferulylmethane, Natural Yellow 3) is responsible for the colour of turmeric and the colour change upon change in pH. In one embodiment of the invention the pH-indicator substance is curcumin. Curcumin according to the invention may be from any source e.g. derived from turmeric. Curcumin has a yellow colour at pH values below about pH 8 and undergoes a colour shift to a red colour when pH is raised above about pH 8. If pH is raised further above about pH 11 curcumin undergoes a further colour shift from red to an orange colour. Curcumin, e.g. in the form of turmeric, may be combined with one or more additional pH indicator substances.

In other embodiments the pH indicator is phenol red, bromthymol blue, methyl red, neutral red, bromcresol green, methylene blue, or any combination thereof, such as e.g. the combination of bromcresol green and methyl red, or the combination of methylene blue and neutral red.

Preparation of Swatch

One aspect of the invention relates to the preparation of a swatch according to the invention. In one embodiment of the invention a swatch is prepared by impregnating a piece of fabric with the desired substrate and pH indicator. Impregnation may be performed by any suitable method, e.g. by spraying the substrate and/or pH indicator onto the fabric or by immersion of the fabric in a solution of the substrate and/or the pH indicator. If the substrate and/or indicator is applied as a solution, the swatch may be dried after application. The substrate and pH indicator should be applied in a way suitable to obtain a uniform coverage of the fabric. The substrate and pH indicator may be mixed before impregnating the fabric, in any way appropriate to obtain a homogenous mixture. The mixture may e.g. be filtered. In one embodiment of the invention cream and turmeric is mixed, e.g. at 30-60° C., and applied to a fabric by immersion of the fabric in the cream-turmeric mix. The cream-turmeric mix may be filtered before application to the fabric to remove any undesired particles and obtain a uniform mixture.

Assay of Washing Performance

The swatch of the invention may be used for testing the washing performance of an enzyme that is able to act on the substrate impregnated in the swatch resulting in a change of pH. This may e.g. be done by contacting the swatch with the enzyme, rinsing the swatch with water, and measuring the colour intensity, remission, or fluorescence of the swatch at one or more wavelengths before and after contact with the enzyme. Washing performance may then be assessed by comparing colour intensity of the intact swatch and of the swatch after contact with the enzyme. The enzyme will usually be in an aqueous solution when contacting it with the swatch. An aqueous solution may additionally contain other components, e.g. salts.

Cleaning and Detergent Compositions

It will often be desirous to assay the performance of the enzyme in an actual detergent solution, such a solution may comprise additional compounds known to be incorporated in detergent compositions such as enzymes and/or enzyme stabilizers, inhibitors, enhancers, co-factors, builders, builder systems, bleach systems, bleach activators, metal-containing bleach catalyst, optical brighteners, nonionic-, anionic-, cationic-, zwitterionic and amphoteric surfactants, fabric softening agents, softening clays, clay flocculants, dye-transfer inhibiting agents, polymeric soil release agents, clay soil removal agents, anti-soil redeposition agents, polymeric dispersing systems, chelating agents, alkoxylated polycarboxylates, perfumes, perfume systems, carrier systems, dyes and pigments, fabric care agents, color care agents, and the like. The pH of the solution may be adjusted to any appropriate value, e.g. a value close to, or in, the range of pH-values wherein the colour of the pH indicator of the swatch is affected.

In general, cleaning and detergent compositions are well described in the art and reference is made to WO 96/34946; WO 97/07202; WO 95/30011 for further description of suitable cleaning and detergent compositions.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanol-amide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylene-diaminetetraacetic acid, diethylenetriaminepentaacetic acid, alkyl- or alkenyl-succinic acid, soluble silicates or layered silicates (e.g. SKS-6 from Hoechst).

The detergent may comprise one or more polymers. Examples are carboxymethyl-cellulose, poly(vinylpyrrolidone), poly (ethylene glycol), poly(vinyl alcohol), poly(vinyl-pyridine-N-oxide), poly(vinylimidazole), polycarboxylates such as poly-acrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

Variations in local and regional conditions, such as water hardness and wash temperature calls for regional detergent compositions. Detergent Examples 1 and 2 provide ranges for the composition of a typical Latin American detergent and a typical European powder detergent respectively.

DETERGENT EXAMPLE 1

Typical Latin American Detergent Composition

| Group | Subname | Content |
|---|---|---|
| Surfactants | | 0-30% |
| | Sulphonates | 0-30% |
| | Sulphates | 0-5% |
| | Soaps | 0-5% |
| | Non-ionics | 0-5% |
| | Cationics | 0-5% |
| | FAGA | 0-5% |
| Bleach | | 0-20% |
| | SPT/SPM | 0-15% |
| | NOBS, TAED | 0-5% |
| Builders | | 0-60% |
| | Phosphates | 0-30% |
| | Zeolite | 0-5% |
| | $Na_2OSiO_2$ | 0-10% |
| | $Na_2CO_3$ | 0-20% |
| Fillers | | 0-40% |
| | $Na_2SO_4$ | 0-40% |
| Others | | up to 100% |
| | Polymers | |
| | Enzymes | |
| | Foam regulators | |
| | Water | |
| | Hydrotropes | |
| | Others | |

DETERGENT EXAMPLE 2

Typical European Powder Detergent Composition

| Group | Subname | Content |
|---|---|---|
| Surfactants | | 0-30% |
| | Sulphonates | 0-20% |
| | Sulphates | 0-15% |
| | Soaps | 0-10% |
| | Non-ionics | 0-10% |
| | Cationics | 0-10% |
| | Other | 0-10% |
| Bleach | | 0-30% |
| | SPT/SPM | 0-30% |
| | NOBS + TAED | 0-10% |
| Builders | | 0-60% |
| | Phosphates | 0-40% |
| | Zeolite | 0-40% |
| | $Na_2OSiO_2$ | 0-20% |
| | $Na_2CO_3$ | 0-20% |
| Fillers | | 0-40% |
| | $Na_2SO_4$ | 0-40% |
| | NaCl | 0-40% |
| Others | | up to 100% |
| | Polymers | |
| | Enzymes | |
| | Foam regulators | |
| | Water | |

| Group | Subname | Content |
| --- | --- | --- |
| | Hydrotropes | |
| | Others | |

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

It is at present contemplated that in the detergent compositions any single enzyme, in particular the enzyme of the invention, may be added in an amount corresponding to 0.005-200 mg of enzyme protein per litre of wash liquor, preferably 0.025-50 mg of enzyme protein per litre of wash liquor, in particular 0.05-10 mg of enzyme protein per litre of wash liquor.

Wash Performance Test

Contacting the swatch with the enzyme will usually be performed by wetting the swatch with an aqueous solution of the enzyme. Wetting may be done in any appropriate way, e.g. by spraying, or immersion of the swatch with an aqueous solution of the enzyme. Contact and rinsing may be performed by washing the swatch with the aqueous solution of the enzyme in a conventional washing process, e.g. in a conventional washing machine. Contact between the swatch and the enzyme may be performed at any appropriate temperature and for any appropriate time for testing the washing performance of an enzyme, e.g. at 20-90° C. for e.g. 10-120 minutes. Contact between the swatch and the enzyme may e.g. be performed for a time sufficient to obtain a measurable washing effect. During contact between the swatch and the enzyme, the swatch and enzyme may be subjected to mechanical treatment, e.g. shaking, rotation, or the like, e.g. to simulate the mechanical treatment in a conventional laundry machine. The swatch may be rinsed after contacting with the enzyme, e.g. 1-3 times, as is usual in a conventional washing process.

The colour intensity of the swatch may be evaluated while the swatch is still wet, or the swatch may be dried. Since some enzyme may still be present on the swatch even after rinsing and may lead to additional breakdown of the substrate during drying, it may be preferred to perform drying at a high temperature where the enzyme is inactivated and where drying is achieved within the shortest possible time, to ensure that the effect that is assayed is due to the action of the enzyme before the drying step, and not during the drying step.

In some circumstances it may be desired to assay the activity of the remaining enzyme during the drying step. E.g. it is known that lipases may remain in clothes even after rinsing and may be active during drying of clothes after wash. This effect may be desirous, or it may be un-desirous since it in some instances may lead to the formation of malodour. In one embodiment the invention relates to a method for assaying the activity of an enzyme during drying. This may be performed by measuring the colour intensity before and after drying and comparing these. The drying may be performed in any suitable way. The performance of the enzyme during wash and the activity during drying may be tested on the same swatch by measuring colour intensity both before washing, after rinse and after drying.

The contact between the swatch and enzyme may e.g. be conducted in an Automated Mechanical Stress Assay (AMSA) as described in WO 02/42740. With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress.

Detergents

Detergents without enzyme activity for wash performance tests of enzymes with the swatch of the invention can be obtained by purchasing fully formulated commercial detergents at the market and subsequently inactivating the enzymatic components by heat treatment (5 minutes at 85° C. in aqueous solution). Moreover a commercial detergent base without enzymes can be purchased directly from the manufacturer. Further a suitable model detergent can be composed according to the description herein. The enzyme(s) to be tested with the swatch can then be added to the detergent/detergent base for testing.

Colour Measurement

In one embodiment the performance of the enzyme is measured as the difference in colour intensity of the textile samples contacted with that specific enzyme. The difference may be assessed visually, e.g. by comparing colour and intensity with a number of prepared standards, or it may be e.g. assessed by measuring reflectance at one or more wavelengths, e.g. with a conventional scanner attached to a PC. Dedicated equipment for measuring colour and/or reflectance may also be used for assessing the change in colour and intensity.

The colour intensity may e.g. be measured at a number of different wavelengths, e.g. red, green and blue, and an intensity value (Int) may be calculated, e.g. by adding the RGB values together as vectors and then taking the length of the resulting vector:

$$Int = \sqrt{r^2 + g^2 + b^2}$$

The wavelength(s) used for detecting the colour change may be chosen in accordance with the colour characteristics of the pH indicator(s) used. The wavelength(s) best suited in relation to a specific pH indicator or combination of pH indicators may be determined by the skilled person by routine experimentation.

EXAMPLES

Lipases 2 commercial lipases (Lipex® and Lipolase®, both from Novozymes A/S, Bagsvaerd, Denmark) and 5 experimental lipases (indicated as Lipase ID no. 1-5) were used in the experiments.

Cream-Turmeric Swatches

Cream-turmeric swatches were prepared by mixing 5 g of turmeric (Santa Maria, Denmark) with 100 g cream (38% fat, not homogenised, Arla, Denmark) at 50° C., the mixture was left at this temperature for 20 minutes and filtered to remove any undissolved particles. Woven cotton swatches were immersed in the cream-turmeric mixture and afterwards allowed to dry at room temperature over night and frozen until use.

Cream-Phenol Red Swatches

Cream-phenol red swatches were prepared by mixing 22 mg of phenol red (Aldrich no. 11, 452-9) with 100 g cream (38% fat, not homogenised) at 50° C., the mixture was left at this temperature for 20 minutes and filtered to remove any undissolved particles. Woven cotton swatches were immersed in the cream-phenol red mixture and afterwards allowed to dry at room temperature over night and frozen until use.

Cream-Bromthymol Blue Swatches

Cream-bromthymol blue swatches were prepared by mixing 25.3 mg of bromthymol blue (BDH Chemicals LTD. no. 20020) with 100 g cream (38% fat, not homogenised) at 50° C., the mixture was left at this temperature for 20 minutes and filtered to remove any undissolved particles. Woven cotton swatches were immersed in the cream-bromthymol blue mixture and afterwards allowed to dry at room temperature over night and frozen until use.

Cream-Methylene Blue/Neutral Red Swatches

Cream-methylene blue/neutral red swatches were prepared by mixing 13.2 mg of methylene blue (Merck no. 14279) and 15.0 mg of neutral red (Merck no. 1369) with 100 g cream (38% fat, not homogenised) at 50° C., the mixture was left at this temperature for 20 minutes and filtered to remove any undissolved particles. Woven cotton swatches were immersed in the cream-methylene blue/neutral red mixture and afterwards allowed to dry at room temperature over night and frozen until use.

AMSA (Automated Mechanical Stress Assay)

With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24.

Determination of Colour Change (AMSA)

Colour measurements were made with a professional flatbed scanner (PFU DL2400pro), which is used to capture an image of the washed textile samples. The scans were made with a resolution of 200 dpi and with an output colour dept of 24 bits. In order to get accurate results, the scanner was frequently calibrated with a Kodak reflective IT8 target.

To extract a value for the light intensity from the scanned images, a special designed software application was used (Novozymes Color Vector Analyzer). The program retrieved the 24 bit pixel values from the image and converted them into values for red, green and blue (RGB). The intensity value (Int) was calculated by adding the RGB values together as vectors and then taking the length of the resulting vector:

$$Int = \sqrt{r^2 + g^2 + b^2}$$

The wash performance (P) of the variants was calculated in accordance with the below formula:

$$P = Int(v) - Int(r)$$

where
Int(v) is the light intensity value of textile surface washed with enzyme variant and
Int(r) is the light intensity value of textile surface washed under similar conditions without lipase but with the reference enzyme Lipex.

Miniwash Test

The miniwash test was performed in a computerized robot. The robot consisted of a temperature-controlled water bath, containing 24 wash vessels in which the wash was performed. The swatches were placed and fixed onto racks. Each robot had the capacity for 4 textile racks, which fit into 6 wash vessels, this resulted in six individual textile areas, on which the wash in the tempered wash vessels occurred.

The textile racks were fixed onto two swing arms, and the racks were moved up and down into the wash vessels to mimic an agitation that occurs during a commercial washing. The speed of the mechanical action was set to about 100 up and down movements per minute. After wash, the textile racks were moved to 24 rinse vessels, where the soiled and washed textiles were rinsed. Rinse time was set to 10 minutes. The speed of the mechanical action during rinsing was set to about 60 up and down movements per minute.

Evaluation

Remission of the swatches was measured at 520 nm with Macbeth Color-Eye 7000 remission spectrophotometer. Remission values were calculated as the difference between reference vessel and sample (enzyme) vessel at the chosen wavelength:

$$de\_Rem = Rem_{sample} - Rem_{ref}$$

Tergotometer Wash Test

A Tergotometer instrument was used. The machine consists of four 1.5 litre metal beakers with agitator spindles inserted into the beakers and rotated in a back-and forth manner at a controlled speed (120 rpm), to mimic the type of agitation that occurs in commercial washing. The beakers were immersed in a temperature controlled water bath. Each beaker was filled with 1 litre of detergent solution. Test swatches were added to each beaker. After a wash period of 14 minutes, the swatches were promptly removed from the beakers and rinsed thoroughly with water. Remission was measured as described under Miniwash.

Example 1

Colour Change of Cream-Turmeric Swatch as Function of pH

A buffer stock solution was prepared according the Table below:

| | Buffer stock solutions | Final concentration |
|---|---|---|
| Succinic acid (Sigma S-9512) | 23.62 g/l~0.2M | 0.1M |
| HEPES (Sigma H-3375) | 47.66 g/l~0.2M | 0.1M |
| CHES (Sigma C-2885) | 41.46 g/l~0.2M | 0.1M |
| CAPS (Serva no. 17674) | 44.26 g/l~0.2M | 0.1M |
| CaCl$_2$ (Merck no. 2382) | 0.294 g/l~2 mM | 1 mM |
| KCl (Merck no. 1.04936) | 22.37 g/l~0.3M | 0.15M |
| Triton X-100 (Sigma T-9284) | 0.2 g/l~0.02% | 0.01% |

500 ml of stock solution was prepared. For each pH, 25 ml of the stock solution was adjusted to the desired pH (pH 5.5-pH 6.0-pH 6.5-pH 7.0-pH 7.5-pH 8.0-pH 8.5-pH 9.0-pH 9.5-pH 10.0-pH 10.5-pH 11.0) with NaOH or HCl, respectively. Subsequently, the volume of each buffer was adjusted to 50 ml.

Cream-turmeric swatch prepared as described above was subjected to the buffers in an AMSA test at 30° C. for 5 minutes. The swatches were scanned and intensity determined as described above. The results are shown in FIG. 1. It can be seen that the colour shift of turmeric occurs mainly between pH 7 and 8.

Example 2

AMSA Tests

Assays of the washing effect of a number of lipases were conducted under the experimental conditions specified below:

Assay A

| | |
|---|---|
| Commercial detergent base | European powder type |
| Detergent dosage | 4 g/l |
| Test solution volume | 160 micro I |
| pH | as it is in detergent (app. 10-10.5) |
| Wash time | 20 min. |
| Temperature | 30° C. |
| Water hardness | 15° dH |
| Enzyme concentration in test solution | 0.025-0.05-0.1-0.25-0.5-1-2-4 mg enzyme protein/L |
| Test material | Cream/Turmeric swatch |

The European powder type detergent was composed according to the description herein. Water hardness was adjusted to 15° dH by addition of $CaCl_2*2H_2O$; $MgCl_2*6H_2O$; $NaHCO_3$ ($Ca^{2+}:Mg^{2+}:HCO^{3-}=4:1:7.5$) to the test system. After washing the textile pieces were flushed in tap water and dried.

Assay B

| | |
|---|---|
| Commercial detergent base | Latin American powder type |
| Detergent dosage | 2.4 g/l |
| Test solution volume | 160 micro I |
| pH | as it is in detergent (app. 10-10.5) |
| Wash time | 20 min. |
| Temperature | 25° C. |
| Water hardness | 12° dH |
| Enzyme concentration in test solution | 0.025-0.05-0.1-0.25-0.5-1-2-4 mg enzyme protein/L |
| Test material | Cream/Turmeric swatch |

The Latin American type detergent was composed according to the description herein. Water hardness was adjusted to 12° dH by addition of $CaCl_2*2H_2O$; $MgCl_2*6H_2O$; $NaHCO_3$ ($Ca^{2+}:Mg^{2+}:HCO^{3-}2:1:4.5$) to the test system. After washing the textile pieces were flushed in tap water and dried.

pH in Wash Liquor

Figure 2:
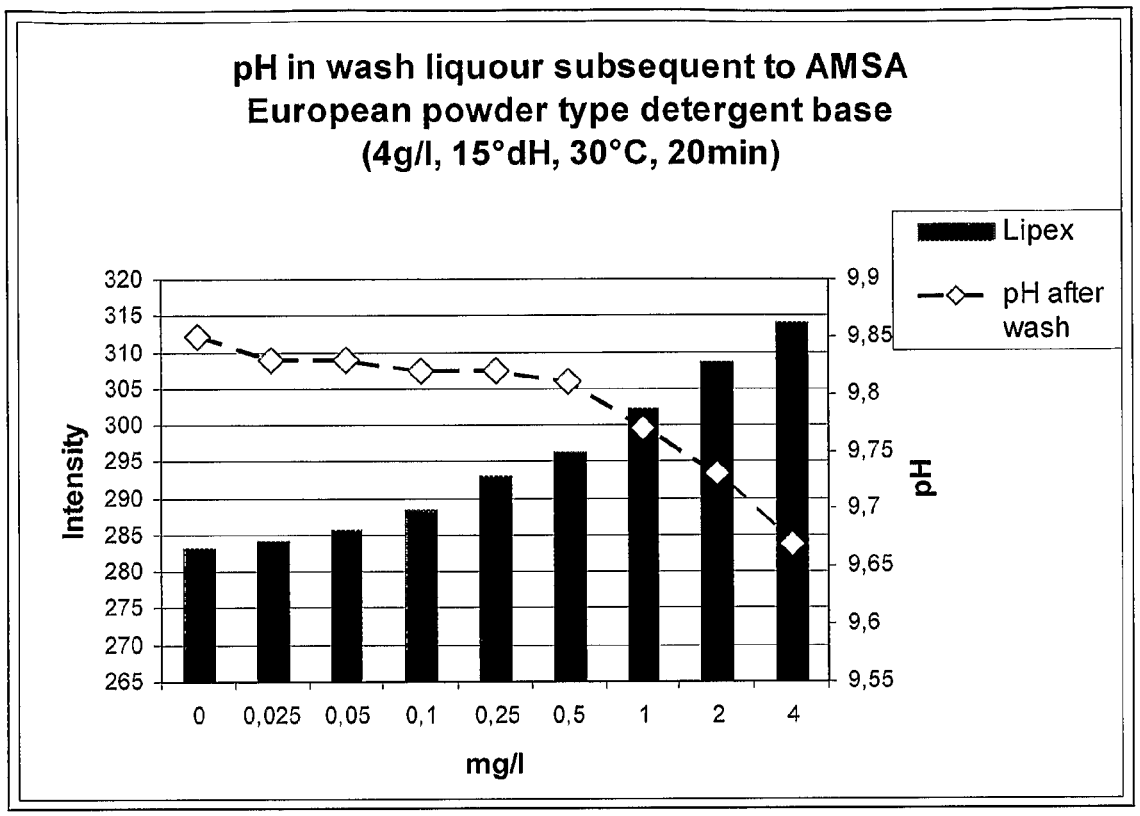
FIG. 2 shows Cream/turmeric swatch after AMSA of Lipex in 4g/l of European powder type detergent base at 15° dH and 30° C. 0.025-0.05-0.1-0.25-0.5-1-2-4 mg Enzyme Protein per liter (ppm) of Lipex were used in this dose-response experiment. The pH of the wash liquor was measured immediately after the wash.

FIG. 2 shows the results of an experiment according to Assay A with Lipex, wherein the pH of the washing liquid was determined immediately after the wash. Colour intensity was measured on the wet swatches. It is seen that the pH only changes slightly in the washing liquid, whereas the colour change indicates a pH decrease locally on the swatch of at least two pH units.

Colour Change as Affected by Drying Conditions

Figure 3:
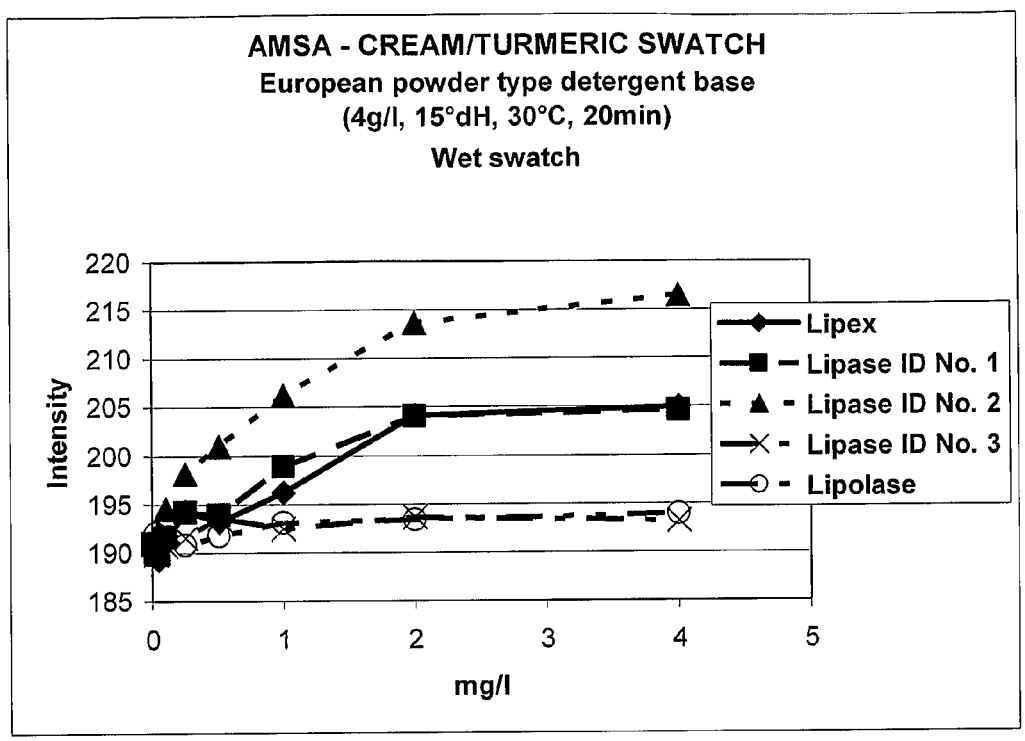
FIG. 3-6 show AMSA of Lipase variants in 4 g/l of European powder type detergent base at 15° dH and 30° C. 0.025-0.05-0.1-0.25-0.5-1-2-4 mg Enzyme Protein per liter (ppm) of each of the enzymes were used in this dose-response experiment. Swatches were scanned directly after wash and rinsed in a wet state (results shown in FIG. 3), after they have been dried at 60° C. for 7 min (results shown in FIG. 4), after they have been dried at 85° C. for 5 min (results shown in FIG. 5). Alternatively, swatches were dried at 20° C. for 1 hour (results shown in FIG. 6).

FIGS. 3-6 show the results of experiments according to Assay A wherein drying was conducted in various ways after rinsing:

FIG. 3 shows the results of colour measurement on the wet swatches without drying.

Figure 4:
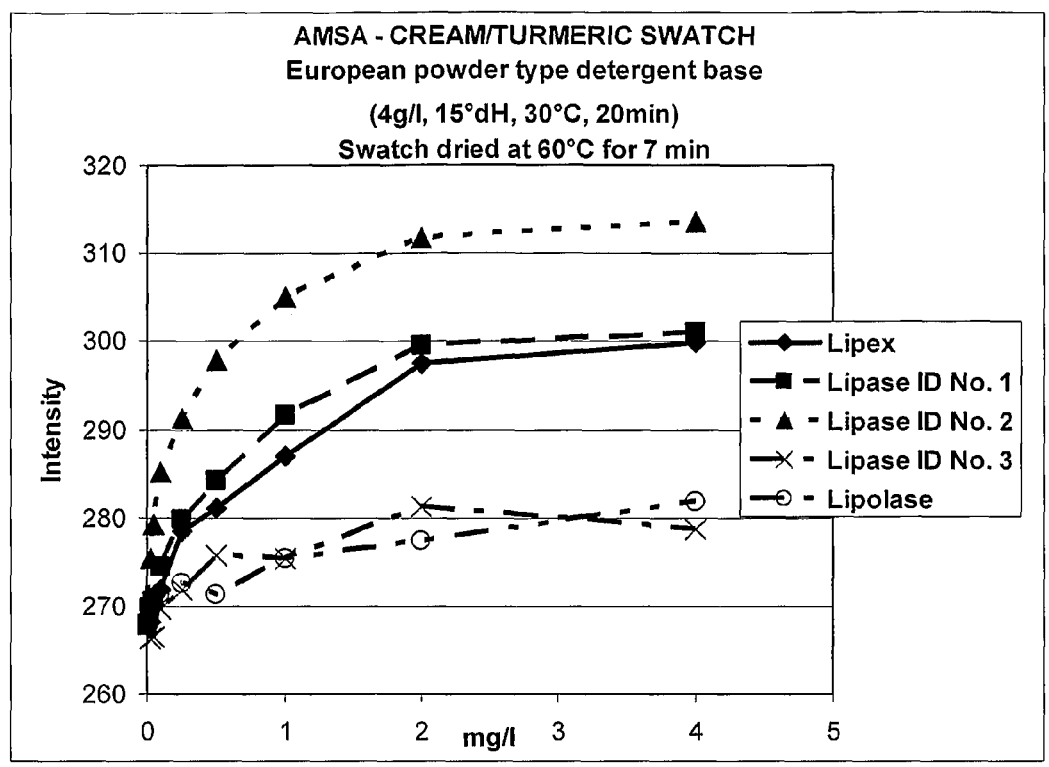

FIG. 4 shows the results of colour measurement after drying at 60° C. for 7 minutes.

Figure 5:
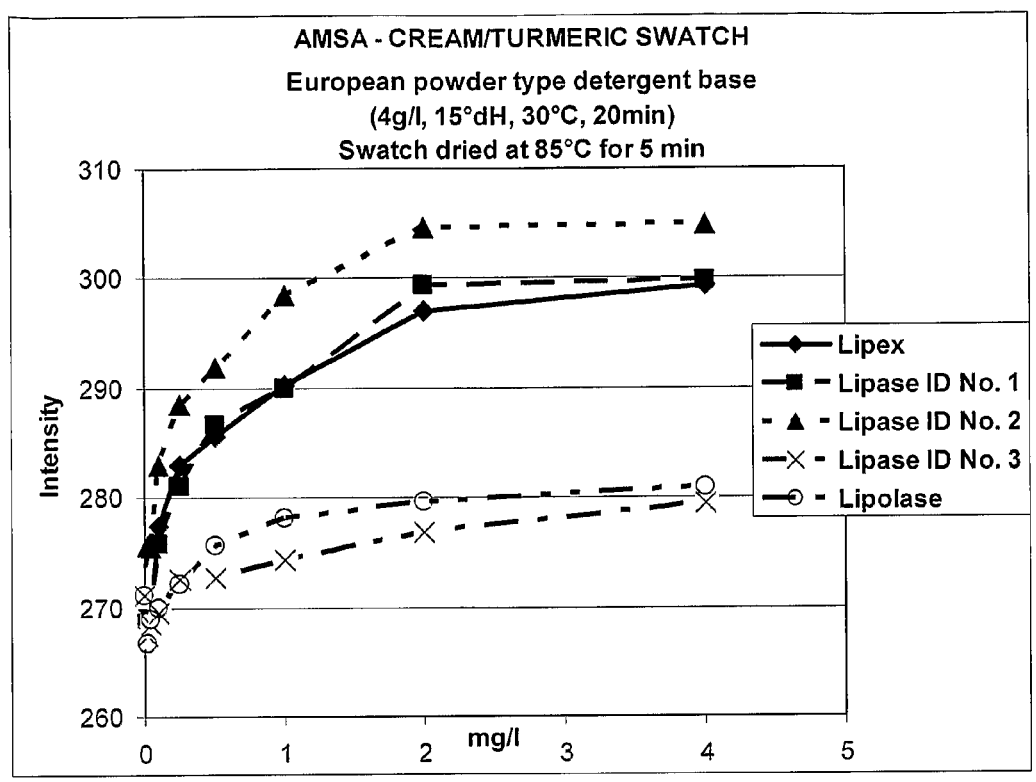
Figure 6:
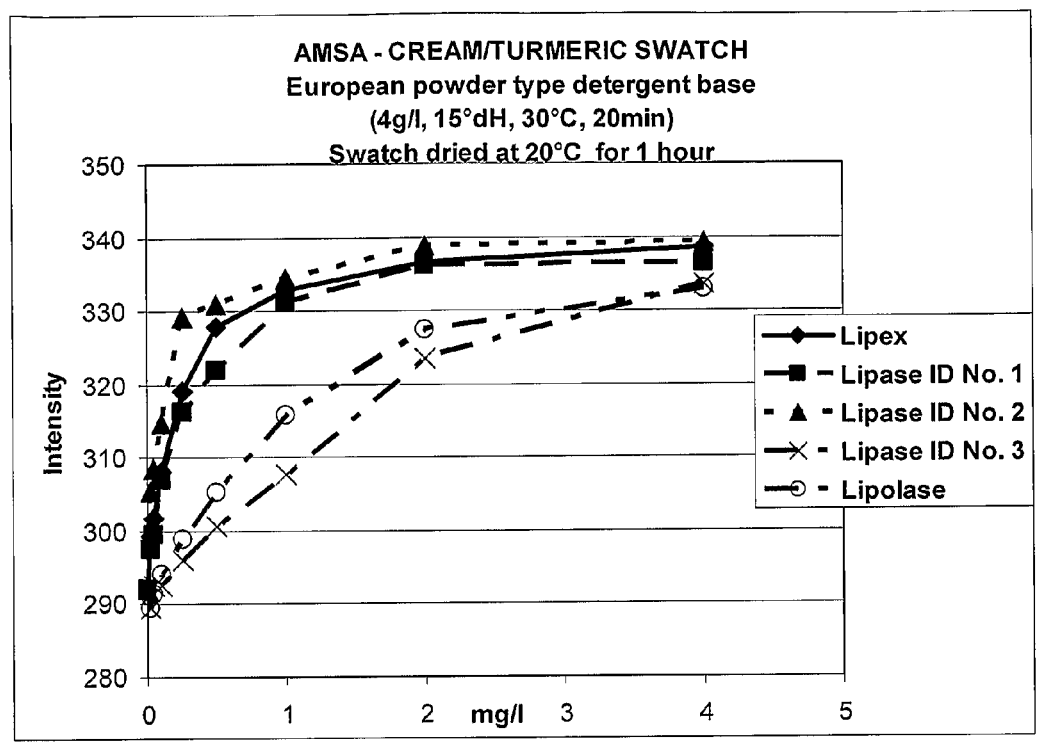

FIG. 5 shows the results of colour measurement after drying at 85° C. for 5 minutes FIG. 6 shows the results of colour measurement after drying at 20° C. for 1 hour.

By comparing FIGS. 4-6 with FIG. 3, the effect of lipase activity during drying can be determined.

Colour Change as Effected by Detergent Composition

Figure 7:
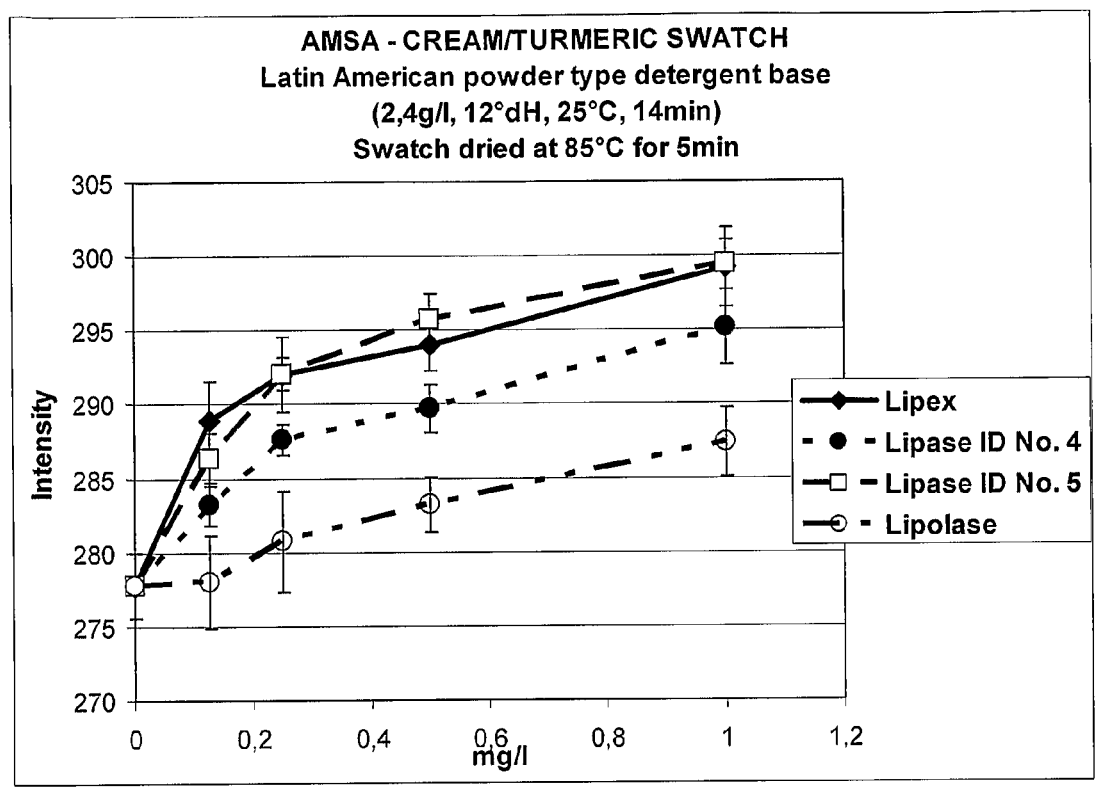
FIG. 7 shows AMSA of Lipase variants in 2.4 g/l of Latin American type powder type detergent base at 12° dH and 25° C. 0.125-0.25-0.5-1 mg Enzyme Protein per liter (ppm) of each of the enzymes were used in this dose-response experiment. Swatches were scanned after wash and after they had been dried at 85° C. for 5 minutes.
Figure 8:
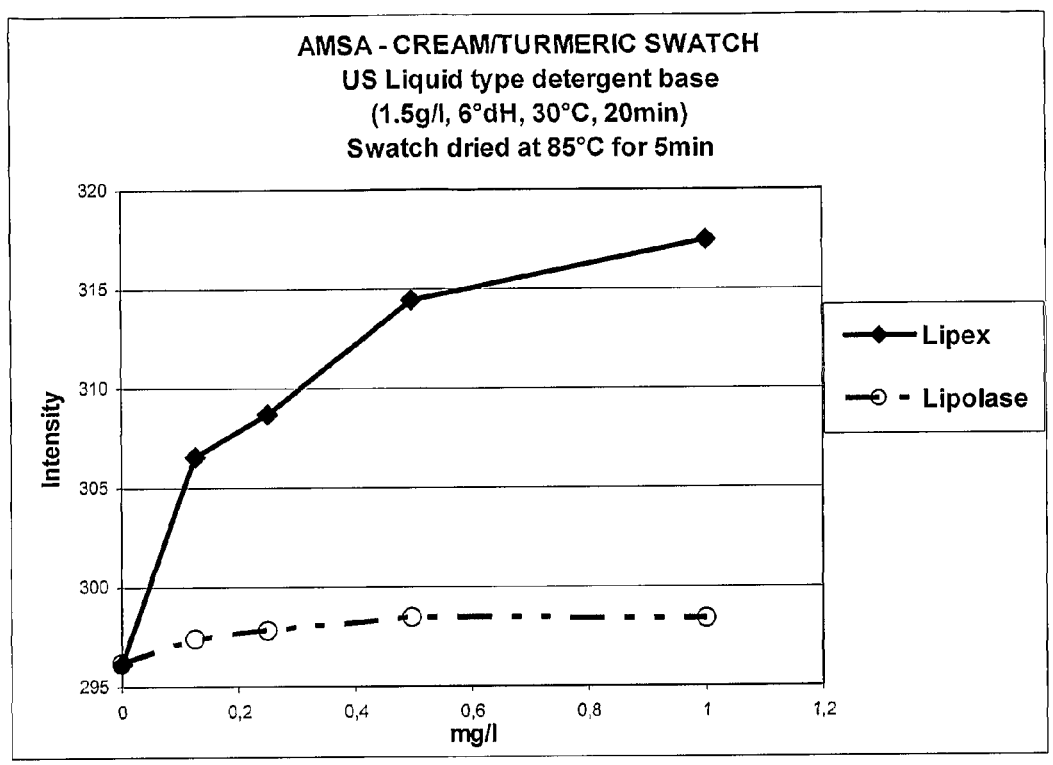
FIG. 8 shows AMSA of Lipase variants in 1.5 g/l of US Liquid type detergent base at 6° dH and 30° C. 0.125-0.25-0.5-1 mg Enzyme Protein per liter (ppm) of each of the enzymes were used in this dose-response experiment. Swatches were scanned after wash and after they had been dried at 85° C. for 5 minutes.

FIG. 7 shows results of experiments according to Assay B (Latin American powder type detergent), and FIG. 8 shows results of experiments with a US liquid type detergent. In both cases swatches were dried at 85° C. for 5 minutes.

Effect of pH Indicator

Figure 9:
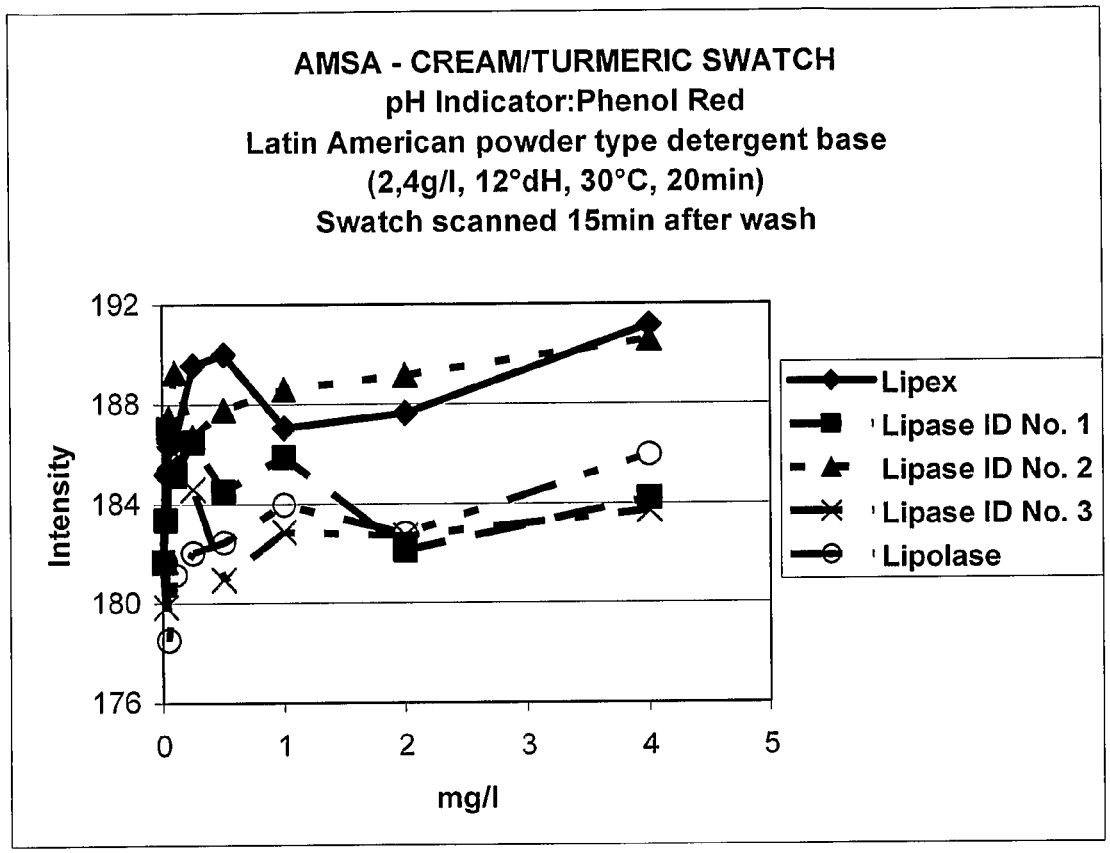
FIG. 9 shows AMSA with Cream-Phenol Red swatch of Lipase variants in 2.4 g/l of Latin American type powder type detergent base at 12° dH and 25° C. 0.5-1-2-4 mg Enzyme Protein per liter (ppm) of each of the enzymes were used in this dose-response experiment. Swatches were scanned 15 minutes after wash.
Figure 10:
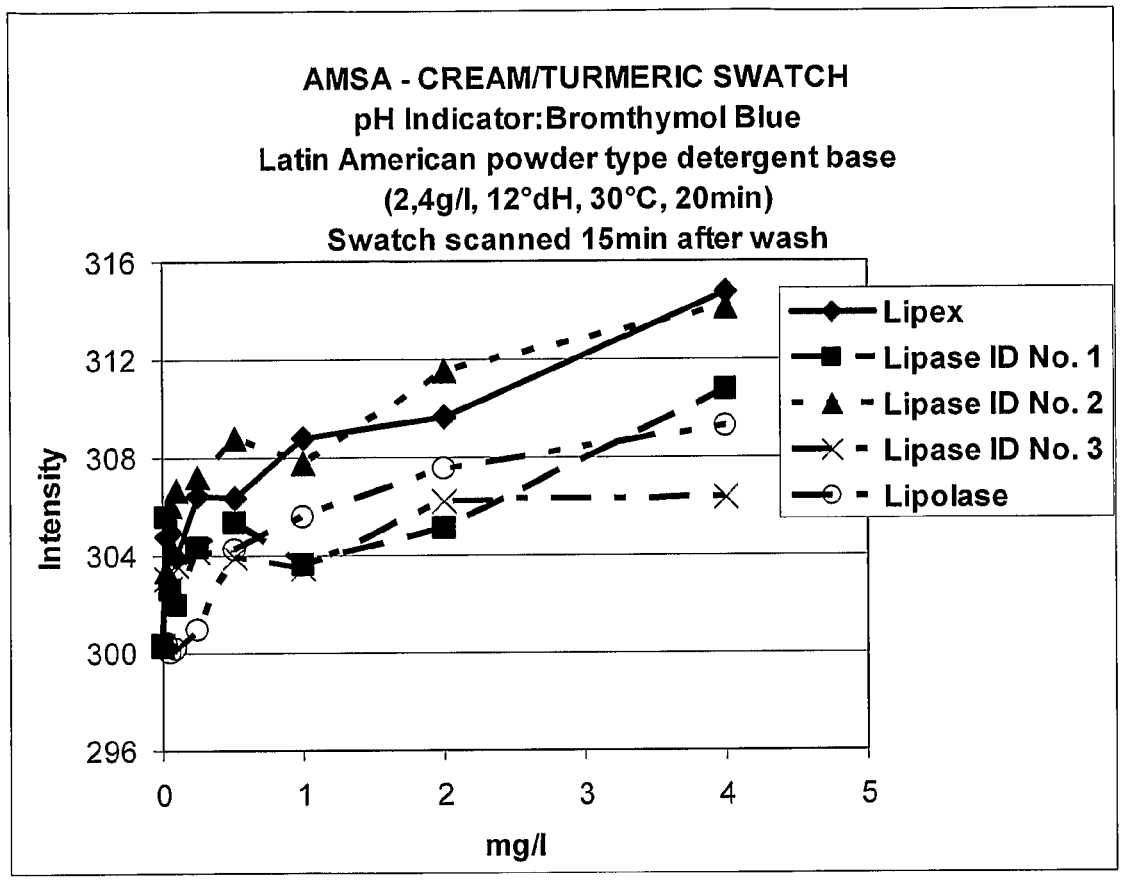
FIG. 10 shows AMSA with Cream-Bromthymol Blue swatch of Lipase variants in 2.4 g/l of Latin American type powder type detergent base at 12° dH and 25° C. 0.5-1-2-4 mg Enzyme Protein per liter (ppm) of each of the enzymes were used in this dose-response experiment. Swatches were scanned 15 minutes after wash.
Figure 11:
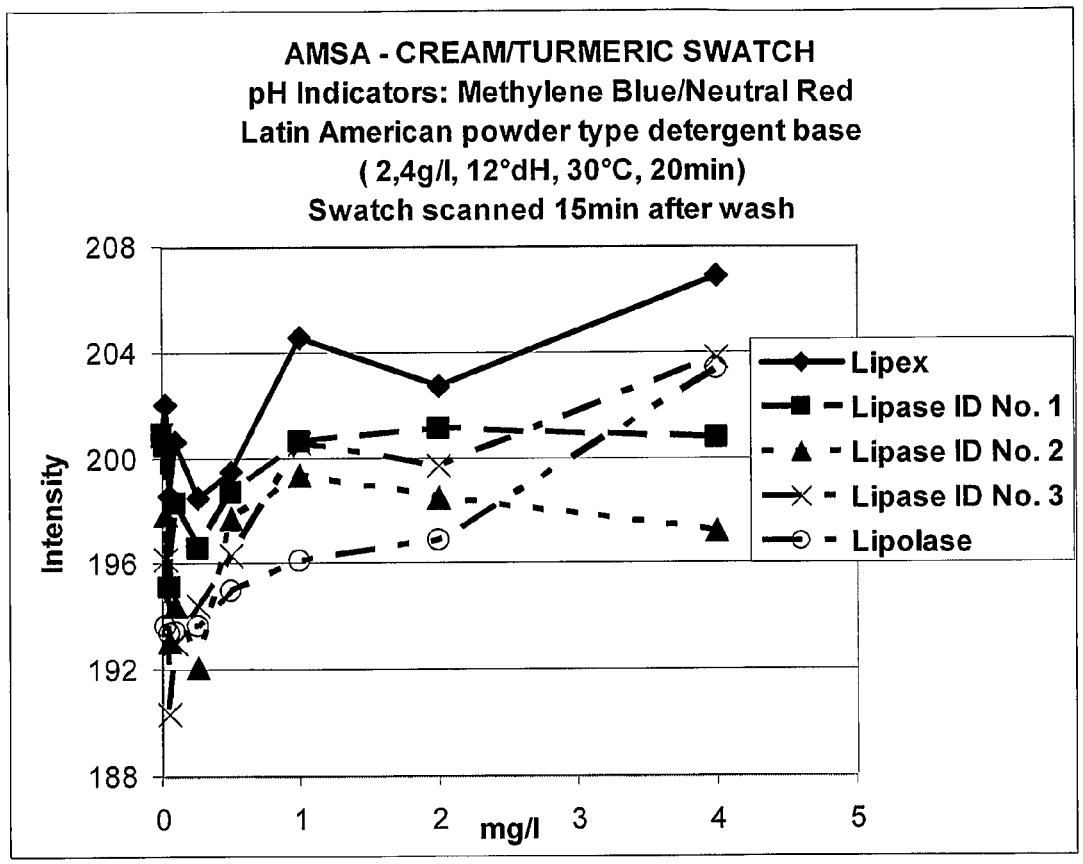
FIG. 11 shows AMSA with Cream-Methylene Blue/Neutral Red swatch of Lipase variants in 2.4 g/l of Latin American type powder type detergent base at 12° dH and 25° C. 0.5-1-2-4 mg Enzyme Protein per liter (ppm) of each of the enzymes were used in this dose-response experiment. Swatches were scanned 15 minutes after wash.

FIG. 9 shows results of experiments with cream-phenol red swatches, FIG. 10 shows results of experiments with cream-bromthymol blue swatches, and FIG. 11 shows results of experiments with cream-methylene blue/neutral red swatches. In all cases experiments were conducted according to Assay B and colour was measured on wet swatches 15 minutes after rinsing.

Example 3

Miniwash Test

Wash performance of a number of lipases were determined in the Miniwash test on cream-turmeric swatches under the following conditions.

| | |
|---|---|
| Commercial detergent base | Latin American powder type |
| Detergent dosage | 2.4 g/l |
| Test solution volume | 200 ml |
| pH | as it is in detergent (app. 10-10.5) |
| Wash time | 14 min. |
| Temperature | 25° C. |
| Water hardness | 12° dH |
| Enzyme concentration in test solution | 0.125-0.25-0.5-1 mg enzyme protein/L |
| Test material | Cream/Turmeric swatch |

The Latin American type detergent was composed according to the description herein. Water hardness was adjusted to 12° dH by addition of $CaCl_2*2H_2O$; $MgCl_2*6H_2O$; $NaHCO_3$ ($Ca^{2+}:Mg^{2+}:HCO^{3-}2:1:4.5$) to the test system. After washing the textile pieces were flushed in tap water and dried at 85° C. for 5 minutes.

Figure 12:
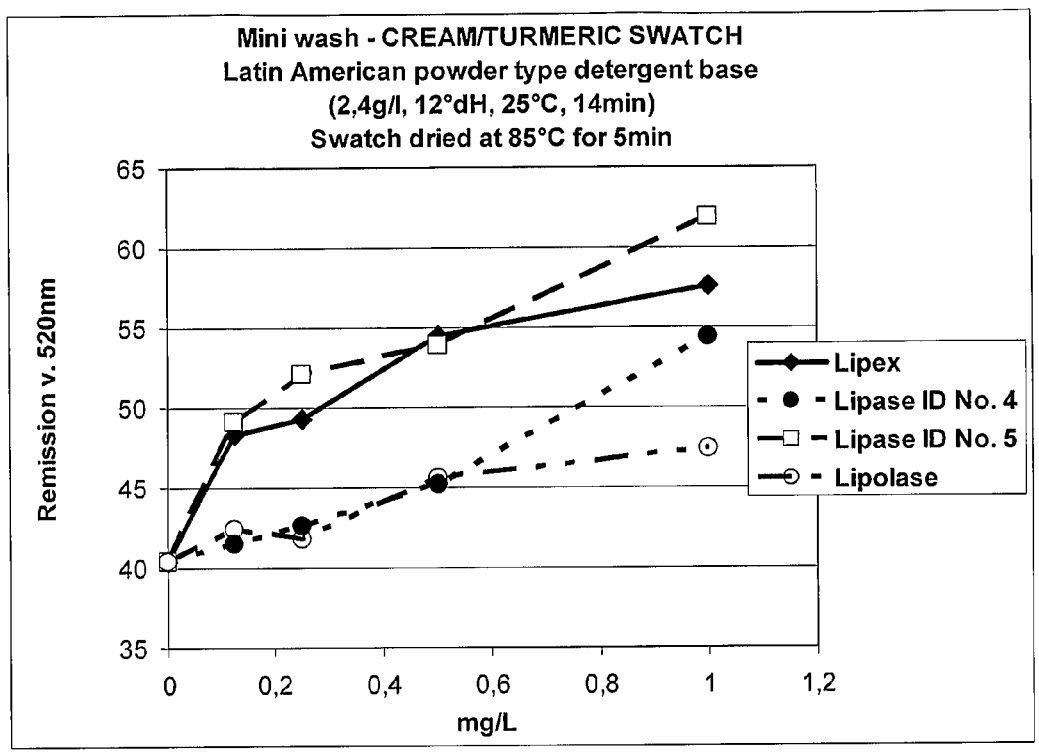
FIG. 12 shows Mini wash of Lipase variants in 2.4 g/l of Latin American type powder type detergent base at 12° dH and 25° C. 0.125-0.25-0.5-1 mg Enzyme Protein per liter (ppm) of each of the enzymes were used in this dose-response experiment. Swatches were scanned after wash and after they had been dried at 85° C. for 5 minutes.

Results are shown in FIG. 12.

Example 4

Tergotometer Wash Test

Wash performance of a number of lipases were determined in the Tergotometer wash test on cream-turmeric swatches under the following conditions.

| | |
|---|---|
| Commercial detergent base | Latin American powder type |
| Detergent dosage | 2.4 g/l |
| Test solution volume | 1000 ml |
| pH | as it is in detergent (app. 10-10.5) |
| Wash time | 14 min. |
| Temperature | 25° C. |
| Water hardness | 12° dH |
| Enzyme concentration in test solution | 0-0.25-1 mg enzyme protein/L |
| Test material | Cream/Turmeric swatch |

The Latin American type detergent was composed according to the description herein. Water hardness was adjusted to 12° dH by addition of $CaCl_2*2H_2O$; $MgCl_2*6H_2O$; $NaHCO_3$ ($Ca^{2+}$:$Mg^{2+}$:$HCO^{3-}$ 2:1:4.5) to the test system. After washing the textile pieces were flushed in tap water and dried at 85° C. for 5 minutes.

Figure 13:
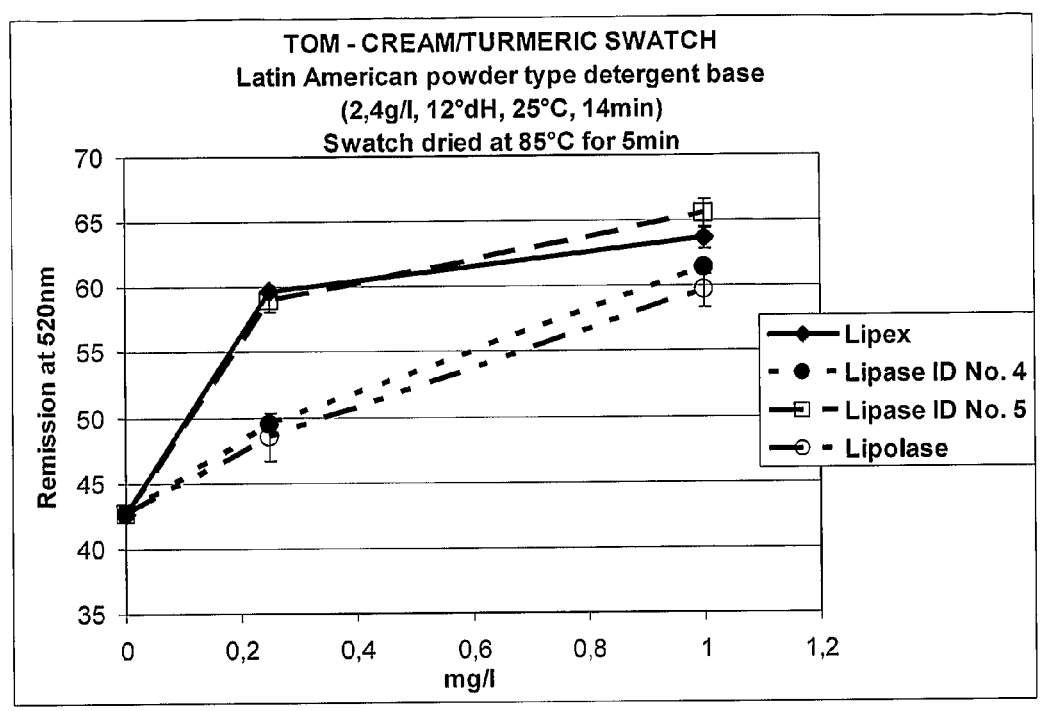
FIG. 13 shows Tergotometer wash of Lipase variants in 2.4 g/l of Latin American type powder type detergent base at 12° dH and 25° C. 0.125-0.25-0.5-1 mg Enzyme Protein per liter (ppm) of each of the enzymes were used in this dose-response experiment. Swatches were scanned after wash and after they had been dried at 85° C. for 5 minutes.

Results are shown in FIG. 13.

The invention claimed is:

1. A swatch for testing the washing performance of an enzyme, comprising a pH-indicator substance and a substrate for the enzyme, wherein conversion of the substrate by the enzyme will lead to a change in pH locally on the swatch.

2. A swatch according to claim 1 wherein the substrate is triglyceride.

3. A swatch according to claim 1 comprising milk fat.

4. A swatch according to claim 3 comprising cream.

5. A swatch according to claim 1 for testing the washing performance of an enzyme with lipase activity.

6. A swatch according to claim 1 comprising protein.

7. A swatch according to claim 6 for testing the washing performance of an enzyme with proteolytic activity.

8. A swatch according to claim 1 comprising curcumin.

9. A swatch according to claim 1 comprising turmeric.

10. A swatch according to claim 1 comprising one or more of phenol red, bromthymol blue, methyl red, neutral red, bromcresol green, and methylene blue.

11. Method for preparing a swatch according to claim 1 comprising impregnating a swatch with a substrate and a pH-indicator substance.

12. Method for testing the washing performance of an enzyme comprising
   a) contacting a swatch according to claim 1 with the enzyme; and
   b) rinsing with water; and
   c) measuring the colour intensity of the swatch at one or more wavelengths before step a) and after step b).

13. Method for testing the activity of an enzyme during drying of a swatch, comprising:
   a) contacting a swatch according to claim 1 with a liquid containing the enzyme; and
   b) rinsing the swatch with water; and
   c) drying the swatch; and
   d) measuring the colour .intensity of the swatch at one or more wavelengths before and after step c).

* * * * *